(12) United States Patent
Waki et al.

(10) Patent No.: US 8,232,436 B2
(45) Date of Patent: Jul. 31, 2012

(54) PROCESS FOR PURIFYING A FLUORINE COMPOUND

(75) Inventors: Masahide Waki, Izumiotsu (JP); Daisuke Sakai, Izumiotsu (JP); Toshihisa Sakurai, Izumiotsu (JP)

(73) Assignee: Stella Chemifa Corporation, Osaka (JP)

( * ) Notice: Subject to any disclaimer, the term of this patent is extended or adjusted under 35 U.S.C. 154(b) by 508 days.

(21) Appl. No.: 12/443,877

(22) PCT Filed: Aug. 29, 2008

(86) PCT No.: PCT/JP2008/065489
§ 371 (c)(1),
(2), (4) Date: Apr. 1, 2009

(87) PCT Pub. No.: WO2009/028640
PCT Pub. Date: Mar. 5, 2009

(65) Prior Publication Data
US 2010/0099931 A1 Apr. 22, 2010

(30) Foreign Application Priority Data
Aug. 31, 2007 (JP) ................... 2007-226285

(51) Int. Cl.
*C07C 17/38* (2006.01)
(52) U.S. Cl. ........................................ 570/177
(58) Field of Classification Search ............. 570/177
See application file for complete search history.

(56) References Cited

U.S. PATENT DOCUMENTS

| | | |
|---|---|---|
| 5,840,266 A | 11/1998 | Lewin |
| 2004/0062696 A1 | 4/2004 | Kikuyama et al. |
| 2006/0219570 A1 | 10/2006 | Furuta et al. |
| 2007/0098624 A1 * | 5/2007 | Luly et al. ............. 423/483 |
| 2010/0099931 A1 | 4/2010 | Waki et al. |

FOREIGN PATENT DOCUMENTS

| | | |
|---|---|---|
| EP | 0 608 087 A2 | 7/1994 |
| EP | 1 380 675 A1 | 1/2004 |
| JP | 5-4801 A | 1/1993 |
| JP | 7-2515 A | 1/1995 |
| JP | 9-268005 A | 10/1997 |
| JP | 2002-241196 A | 8/2002 |
| JP | 2009-057248 A | 3/2009 |
| KR | 2006-100219 | 9/2006 |
| WO | WO 02/063076 A1 | 8/2002 |
| WO | WO 2007/050505 A1 | 5/2007 |

OTHER PUBLICATIONS

Chinese Office Action issued Jan. 30, 2011; Application No. 20008-000066.X; Stella Chemifa Corp.
S.P. Mallela et al.; Contribution from the Department of Chemity, University of Idaho, Mosco; Inorg. Chem. 1988, 27; American Chemical Society; pp. 208-209.
Office Action issued by the Chinese Patent Office on Aug. 26, 2010 for the counterpart Chiniese Patent Application No. 200880000666.X.
Extended European Search Report dated Aug. 4, 2011 in corresponding Application No. 08828553.1.

* cited by examiner

*Primary Examiner* — Jafar Parsa
(74) *Attorney, Agent, or Firm* — Knobbe Martens Olson & Bear LLP

(57) ABSTRACT

Provided is a process for purifying a fluorine compound capable of yielding a highly pure fluorine compound by removing at least oxygen from a fluorine compound containing an oxygen compound as an impurity. In a process according to the present invention for purifying a fluorine compound, the following is brought into contact with the fluorine compound, which contains an oxygen compound as an impurity, thereby removing at least oxygen: carbonyl fluoride in an amount of a 0.1-fold equivalent or more and a 100-fold equivalent or less of oxygen atoms in the fluorine compound.

10 Claims, No Drawings

PROCESS FOR PURIFYING A FLUORINE COMPOUND

This application is the U.S. National Phase under 35. U.S.C. §371 of Internationl Application PCT/JP2008/065489, filed Aug. 29, 2008, which claims priority to Japanese Patent Application No. 2007-226285, filed Aug. 31, 2007. The International Application was published under PCT Article 21(2) in a language other than English.

TECHNICAL FIELD

The present invention relates to a process for purifying a fluorine compound, in which an impurity of an oxygen compound contained in the fluorine compound is simply and easily removed so that the fluorine compound can be purified into a high purity.

BACKGROUND ART

As a process for removing an oxygen compound, as an impurity, which is present in a fluorine compound to purify this compound, there has been hitherto given a method of adding an anhydrous hydrogen fluoride solution to a fluorine compound and repeating the steps of crystallization, solid-liquid separation and drying (see, for example, Patent Documents 1 and 2) a few times. However, the anhydrous hydrogen fluoride solution used in the process is very dangerous, and fastidious care and experience are required. Thus, the process is poor in handleability. Furthermore, this process has a problem that producing costs and the number of steps increase.

Given is also a method of decreasing an oxygen component or carbon component present in a fluorine compound by a fluorine gas (see, for example, Patent Document 3). However, the fluorine gas used in the process is very dangerous, and fastidious care and experience are required. Furthermore, this process includes problems that this process is limited to a case where the fluorine compound is powdery, the process is carried out only at room temperature or higher, and the like.

Patent Document 1: JP-A-05-4801
Patent Document 2: JP-A-09-268005
Patent Document 3: JP-A-2002-241196

DISCLOSURE OF THE INVENTION

Problems to be Solved by the Invention

In light of the above-mentioned problems, the present invention has been made. An object thereof is to provide a process for purifying a fluorine compound capable of yielding a highly pure fluorine compound by removing at least oxygen from a fluorine compound containing an oxygen compound as an impurity.

Means for Solving the Problems

In order to solve the problems in the prior art, the present inventors have investigated a process for purifying a fluorine compound. As a result, the present inventors have found out that carbonyl fluoride exhibits a high reactivity with an oxygen compound in a fluorine compound to generate carbon dioxide, whereby oxygen can be removed from the fluorine compound. Thus, the present invention has been made.

That is, in order to solve the problems, the present invention relates to a process for purifying a fluorine compound, wherein the following is brought into contact with the fluorine compound, which contains an oxygen compound as an impurity, thereby removing at least oxygen: carbonyl fluoride in an amount of a 0.1-fold equivalent or more and a 100-fold equivalent or less of oxygen atoms in the fluorine compound.

Carbonyl fluoride exhibits a high reactivity with an oxygen compound. Accordingly, the carbonyl fluoride is brought into contact with a fluorine compound containing an oxygen compound as an impurity, thereby making it possible to cause the carbonyl fluoride to react with the oxygen compound to generate at least carbon dioxide. According to this manner, the oxygen compound in the fluorine compound can easily be separated as carbon dioxide from the fluorine compound, so that a highly pure fluorine compound can be generated. Here, if the use amount of the carbonyl fluoride is less than a 0.1-fold equivalent of oxygen atoms in the fluorine compound, the reaction thereof with the oxygen compound becomes insufficient so that the removal efficiency of the oxygen atoms lowers. On the other hand, if the use amount is more than a 100-fold equivalent thereof, the machine for the purification becomes large in size and further costs for the production also increase. Thus, these cases are not preferred.

It is preferable that the contact between the fluorine compound and the carbonyl fluoride is performed at a temperature ranging from −50 to 500° C. If the temperature is lower than −50° C., the rate of the reaction between the carbonyl fluoride and the oxygen compound becomes small so that the removal efficiency of the oxygen atoms lowers, and at the same time, the vapor pressure of carbon dioxide generated as a byproduct also lowers so that the separation becomes difficult. Furthermore, it becomes necessary to keep the reactor cool, to use a low-temperature-generating device or the like; and therefore it causes costs for the facilities to increase, so that economical disadvantages are generated. On the other hand, if the temperature is higher than 500° C., the reaction rate becomes large so that the process is efficient. However, it becomes necessary to keep the temperature of the reactor, to use a high-temperature-generating device or the like; and therefore it causes costs for the facilities to increase, so that economical disadvantages are generated.

It is preferable that the fluorine compound is at least one selected from the group consisting of hydrogen fluoride, fluorides of any rare earth element, fluoride salts, and fluoride complex salts.

It is preferable that the contact between the fluorine compound and the carbonyl fluoride is performed by direct contact therebetween in the absence of any solvent.

It is preferable that the carbonyl fluoride is in a gaseous form and is diluted with an inactive gas having a water content of 10 ppm or less to set the content of carbonyl fluoride into the range of 0.01% or more by volume and less than 100% by volume.

It is preferable that the inactive gas is at least one selected from the group consisting of $CO_2$, HF, $N_2$, He, Ne, Ar and dry air. These inactive gases do not exhibit reactivity with the fluorine compound or the carbonyl fluoride gas, and further does not contaminate the fluorine compound.

It is preferable that the contact between the fluorine compound and the carbonyl fluoride is performed at a pressure ranging from 0.2 KPa to 1 MPa. If the pressure is less than 0.2 KPa, an expensive instrument such as a long and large vacuum container or a vacuum generating machine is required so that costs for the production increase. Further, if the pressure is more than 1 MPa, an expensive instrument such as a high-pressure reactor or a high-pressure-generating machine is required so that costs for the production increase.

Effect of the Invention

The present invention exerts effects as described in the following through the above-mentioned means.

That is, according to the present invention, since the carbonyl fluoride exhibits a high reactivity with an oxygen compound, the carbonyl fluoride is brought into contact with a fluorine compound containing an oxygen compound as an impurity, thereby causing the carbonyl fluoride and the oxygen compound to react with each other so that carbon dioxide can be generated. In other words, according to the process of the present invention, an oxygen compound in a fluorine compound is generated as carbon dioxide so that the oxygen compound can easily be separated from the fluorine compound; therefore, a highly pure fluorine compound can be obtained.

BEST MODE FOR CARRYING OUT THE INVENTION

The process for purifying a fluorine compound according to the present invention is performed by bringing the carbonyl fluoride into contact with the fluorine compound, which contains an oxygen compound as an impurity.

Specifically, a fluorine compound containing an oxygen compound as an impurity and the carbonyl fluoride are introduced into a reactor, and an oxygen compound in the fluorine compound and the carbonyl fluoride are caused to react with each other in accordance with a chemical reaction formula illustrated below. This makes it possible to generate at least carbon dioxide, which is an inactive gas, or carbon dioxide and hydrogen fluoride. By separating the carbon dioxide from the fluorine compound, the oxygen atoms are removed. Here, in the chemical formula illustrated below, as the oxygen compound, a compound represented by MxOyHz is given as an example.

$$aM_xO_yH_z + bCOF_2 = bCO_2 + aM_xF_d + cHF$$ [Formula 1]

wherein M represents a metallic element, a nonmetallic element other than oxygen, or ammonia, a, b, c, d, x and z are each a positive integer, and satisfy the following relationships: $1 \leq x \leq 3$, $1 \leq y \leq 10$, $0 \leq z \leq 20$, $d = (2b - c/a)$ and $c = az$.

The oxygen compound that is a target for purification in the present invention means a compound in which a nonmetallic element or metallic element and an oxygen atom are bonded to each other. The nonmetallic element can be exemplified at least one selected from the group consisting of H, B, C, N, Si, P, S, Se and Te. Examples of the metallic element include all elements other than the nonmetallic element, halogens, rare gases and oxygen.

Here, examples of the oxygen compound represented by the MxOyHz exemplified in the chemical formula include oxides such as $CaO$, $MgO$, $Al_2O_3$, $Na_2O$, $K_2O$, $B_2O_3$, $P_2O_5$, $SiO_2$, $GeO_2$, $As_2O_3$, $P_2O_3$, $As_2O_5$, $CuO$ and $FeO$; hydroxides such as $Ca(OH)_2$, $Mg(OH)_2$, $Al(OH)_3$, $NaOH$, $KOH$, $Cu(OH)_2$, $Fe(OH)_2$, $H_3BO_3$, $H_3PO_4$, $H_3PO_3$ and $NH_4OH$; carbonates such as $CaCO_3$, $MgCO_3$, $Al_2(CO_3)_3$, $Na_2CO_3$, $K_2CO_3$, $CuCO_3$ and $FeCO_3$; and hydrogencarbonates such as $Ca(HCO_3)_2$, $Mg(HCO_3)_2$, $NaHCO_3$ and $KHCO_3$.

Further, examples of the oxygen compound other than the oxygen compound represented by MxOyHz include $H_2O$; compounds containing crystal water or bound water, such as $CaCl_2 \cdot 6H_2O$, $MgSO_4 \cdot 7H_2O$, $AlF_3 \cdot 3H_2O$ and $LiBF_4 \cdot H_2O$; and oxygen compounds that react with carbonyl fluoride to generate at least carbon dioxide, such as $POF_3$, $POCl_3$, $POBr_3$, $LiPOF_4$, $LiPO_2F_2$, $LiBF_3(OH)$, $NaPOF_4$, $NaPO_2F_2$, $NaBr_3(OH)$, $KPOF_4$, $KPO_2F_2$, $KBF_3(OH)$, $KPOCl_4$, $KPO_2Cl_2$, $KBCl_3(OH)$, $KPOBr_4$, $KPO_2Br_2$ and $KBBr_3(OH)$.

The fluorine compound is not particularly limited, and examples thereof include fluoride salts such as $AlF_3$, $NH_4F$, $SbF_5$, $SbF_3$, $BaF_2$, $BiF_5$, $CdF_2$, $CaF_2$, $CsF$, $CrF_2$, $CrF_3$, $CoF_2$, $CoF_3$, $CuF_2$, $FeF_2$, $FeF_3$, $GaF_3$, $HfF_4$, $InF_3$, $PbF_2$, $PbF_4$, $LiF$, $MgF_2$, $MnF_2$, $MnF_3$, $NiF_2$, $NbF_5$, $KF$, $RbF$, $AgF_2$, $AgF$, $NaF$, $SnF_4$, $SnF_2$, $SrF_2$, $TaF_5$, $TiF_4$, $VF_4$, $VF_3$, $XeF_2$, $ZnF_2$ and $ZrF_4$; rare earth element fluorides such as $CeF_3$, $DyF_3$, $ErF_3$, $EuF_3$, $GdF_3$, $HoF_3$, $LaF_3$, $LuF_3$, $NdF_3$, $SmF_3$, $PrF_3$, $TbF_3$, $TmF_3$, $YbF_3$ and $YF_3$; fluoride complex salts such as $NH_4F_2$, $NH_4BF_4$, $(NH_4)_3AlF_6$, $(NH_4)_2GeF_6$, $NH_4NbF_6$, $NH_4PF_6$, $(NH_4)_2SiF_6$, $NH_4TaF_6$, $(NH_4)_2TiF_6$, $(NH_4)_2ZrF_6$, $BaSiF_6$, $CsAsF_6$, $Cu(BF_4)_2$, $Fe(BF_4)_2$, $HPF_6$, $H_2ZrF_6$, $Pb(BF_4)_2$, $LiSbF_6$, $LiAsF_6$, $LiPF_6$, $LiBF_4$, $LiCF_3SO_3$, $LiN(CF_3SO_2)_2$, $KHF_2$, $KSbF_6$, $KAsF_6$, $K_2MnF_6$, $KPF_6$, $K_3AlF_6$, $K_2SiF_6$, $K_3NiF7$, $k_2TiF_6$, $K_2ZrF_6$, $KBF_4$, $KCoF_4$, $RbAsF_6$, $RbBF_4$, $AgSbF_6$, $AgAsF_6$, $AgPF_6$, $AgBF_4$, $NaHF_2$, $Na_2SiF_6$, $NaSbF_6$, $Na_3AlF_6$, $NaAsF_6$, $Na_3FeF_6$, $NaPF_6$, $NaTiF_6$, $NaBF_4$ and $ZnSiF_6$; fluoride gases such as $AsF_5$, $AsF_3$, $BF_3$, $CF_4$, $GeF_4$, $MoF_6$, $NF_3$, $PF_5$, $PF_3$, $ReF_6$, $SeF_6$, $SiF_4$, $SF_6$, $TeF_6$ and $WF_6$; and fluoride complex salts or fluoride salts of various organic compounds, such as fluoride complex salts or fluoride salts of a tertiary ammonium or tertiary phosphonium, and among them, examples of the tertiary ammonium cation include such as a tetraalkylammonium cation, an imidazolium cation, a pyrazolium cation, a pyridinium cation, a triazolium cation, a pyridazinium cation, a thiazolium cation, an oxazolium cation, a pyrimidinium cation, and a pyrazinium cation. Furthermore, examples of the tertiary phosphonium cation include such as a tetraalkylphosphonium cation. Further, hydrogen fluoride or the like can be included. Here, the fluorine compound may be used as a hydrogen fluoride solution in which hydrogen fluoride and at least one of the fluorine compounds exemplified above are dissolved.

The use amount of the carbonyl fluoride is from a 0.1-fold equivalent to a 100-fold equivalent of the oxygen atoms in the fluorine compound, preferably from a 0.5-fold equivalent to a 50-fold equivalent thereof, more preferably from a one-fold equivalent to a 10-fold equivalent thereof. If the use amount is less than the 0.1-fold equivalent, the amount of carbonyl fluoride to be caused to react with the oxygen compound is too small so that the removal efficiency of the oxygen atoms lowers. Thus, a sufficient purification effect is not obtained. On the other hand, if the amount is more than the 100-fold equivalent, the amount of the carbonyl fluoride gas becomes excessive so that the costs for the production increase.

The temperature when the fluorine compound and the carbonyl fluoride are brought into contact with each other is preferably from −50 to 500° C., more preferably from 0 to 200° C., in particular preferably from 20 to 150° C. If the temperature is lower than −50° C., the rate of the reaction between the oxygen compound in the fluorine compound and the carbonyl fluoride becomes small so that the removal efficiency of oxygen lowers. Thus, a sufficient purification effect is not obtained. Additionally, the vapor pressure of carbon dioxide, or carbon dioxide and hydrogen fluoride generated as a byproduct or byproducts also lowers so that the separation of the carbon dioxide becomes difficult. Furthermore, it becomes necessary to keep the reactor cool, to use a low-temperature-generating device or the like; and therefore it causes costs for the facilities to increase, so that economical disadvantages are generated. On the other hand, if the temperature is higher than 500° C., the reaction rate becomes large so that the process is efficient. However, it becomes necessary to keep the temperature of the reactor, to use a high-temperature-generating device or the like; and therefore it causes costs for the facilities to increase, so that economical disadvantages are generated.

The pressure when the fluorine compound and the carbonyl fluoride are brought into contact with each other is not particularly limited, and is preferably from 0.2 KPa to 1 MPa, more preferably from 1 KPa to 0.5 MPa. If the pressure is less than 0.2 KPa, an expensive instrument such as a long and large vacuum container or a vacuum generating machine is required so that economical disadvantages are generated. On the other hand, if the pressure is more than 1 MPa, an expensive instrument such as a high-pressure reactor or a high-pressure-generating machine is required so that economical disadvantages are generated.

In a case where the carbonyl fluoride is in a gaseous form, the carbonyl fluoride may be used as it is. It is allowable to properly dilute the carbonyl fluoride for use with an inactive gas to set the content thereof into the range of 0.01 to 100% by volume. The inactive gas may be used without especial limitation as far as the gas is a gas that neither reacts with the fluorine compound, which is a target for the purification, nor the carbonyl fluoride and further does not contaminate the fluorine compound. Specific examples thereof include $CO_2$, HF, $N_2$, Ar, He and dry air, and these may be used alone or in the form of a mixture of two or more thereof. Here, it is preferred that the inactive gas, which is used for the dilution, does not contain such an impurity as reacts with the carbonyl fluoride. In particular, the water content therein is preferably 10 ppm or less, more preferably 1 ppm or less.

About the contact between the fluorine compound and the carbonyl fluoride, they may be brought into direct contact with each other, or the fluorine compound is dissolved or dispersed in an appropriate solvent and the fluorine compound in this state may be brought into contact with the carbonyl fluoride. In the latter case, the contact can be attained by causing bubbling of the carbonyl fluoride gas into a solvent in which the fluorine compound is dissolved or dispersed, or by some other method. The solvent is not particularly limited. It is preferred to use a solvent that does not contaminate the fluorine compound, and in which the solvent itself or an impurity in the solvent does not react with the carbonyl fluoride or the fluorine compound. The impurity is, for example, water. The water content therein is preferably 10 ppm or less, more preferably 1 ppm or less.

The above-mentioned treatment with carbonyl fluoride may be carried out in a batch manner, a continuous manner, or a semi-batch manner. Further, the reactor used for the treatment is not particularly limited, and may be an appropriate reaction of a tank type, a tower type, or the like. Further, in the case of a gas-solid reaction in which the carbonyl fluoride is in a gaseous form and the fluorine compound is in a solid form, or some other case, the use of a fluid bed manner makes it possible to attain the contact between the fluorine compound and the carbonyl fluoride efficiently. Here, in a case where the fluorine compound is in a liquid form or is dissolved in a liquid or the like, a gas-liquid contactor such as a packed column, a plate column or a spray column can be preferably used whether the contactor is in a flow-countering manner or in a flow-parallelizing manner.

In the batch manner or semi-batch manner case, the period in which the fluorine compound and carbonyl fluoride are brought into contact with each other (the treating period) is not particularly limited. It is advisable to set an optimizing period for obtaining the advantageous effect of the purification sufficiently in accordance with the amount of the fluorine compound to be treated, the concentration of the contained oxygen compound, the reaction temperature, the reaction pressure, the concentration of carbonyl fluoride, and the like. Specifically, the period is preferably 1 minute or more and 24 hours or less. If the period is less than 1 minute, the reaction between the carbonyl fluoride and the oxygen compound becomes insufficient so that a sufficient purification effect may not be obtained. On the other hand, if the period is more than 24 hours, the treated amount decreases so that the production costs increase.

As the concentration of the oxygen compound in the fluorine compound is smaller, the concentration is more preferable. Specifically, the oxygen concentration is preferably 10% or less by weight, more preferably 1% or less by weight, in particular preferably 1000 ppm or less by weight. If the oxygen concentration is more than 10% by weight, the use amount of the fluorine compound required for the treatment unfavorably becomes excessive.

As described above, according to the process of the present invention for purifying a fluorine compound, oxygen atoms can be removed from the fluorine compound, which contains an oxygen compound as an impurity, without adopting any especially expensive machine or complicated step.

EXAMPLES

Preferred examples of this invention will be illustratively described in detail hereinafter. However, about materials, blend amounts and others described in the examples, it is not intended that the scope of this invention is limited only thereto unless restrictive description is made. They are mere explanatory examples.

Example 1

First, 300 g of ethylmethylimidazolium $BF_4$ containing 500 ppm of water as an impurity was put into a fluororesin bottle to which a gas intake cock and an exhaust cock were connected.

Next, the gas intake cock was opened to fill, thereinto, 50% by volume $COF_2$ gas, which was diluted with $N_2$ gas having a water content of 1 ppm or less. Thereafter, the cock was closed. The use amount of the $COF_2$ gas was set to a 5-fold equivalent of oxygen atoms in the water.

Furthermore, the fluororesin bottle was soaked into an oil bath, and heated to set the internal temperature to 100° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 100° C. The bottle was again taken out from the oil bath, and the bottle was shaken for one minute to stir the content. This operation was repeated for 30 minutes.

Thereafter, the fluororesin bottle was taken out from the oil bath, and was cooled to room temperature while $COF_2$ gas remaining in the bottle was substituted with $N_2$ gas. After the treatment, the water content in the ethylmethylimidazolium $BF_4$ was measured. As a result, it was 30 ppm.

Comparative Example 1

First, 300 g of ethylmethylimidazolium $BF_4$ containing 500 ppm of water as an impurity was put into a fluororesin bottle to which a gas intake cock and an exhaust cock were connected.

Next, the gas intake cock was opened to fill, thereinto, $N_2$ gas having a water content of 1 ppm or less. Thereafter, the cock was closed.

Furthermore, the fluororesin bottle was soaked into an oil bath, and heated to set the internal temperature to 100° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 100° C. The bottle was again taken out from the oil bath, and the bottle was shaken for one minute to stir the content. This operation was repeated for 30 minutes.

Thereafter, the fluororesin bottle was taken out from the oil bath, and was cooled to room temperature while $N_2$ gas was caused to flow into the bottle. After the treatment, the water content in the ethylmethylimidazolium $BF_4$ was measured. As a result, it was 460 ppm.

Comparative Example 2

First, 300 g of ethylmethylimidazolium $BF_4$ containing 500 ppm of water as an impurity was put into a fluororesin bottle to which a gas intake cock and an exhaust cock were connected.

Next, the bottle was soaked into an oil bath so as to be heated while $N_2$ gas having a water content of 1 ppm or less was caused to flow into the fluororesin bottle at a rate of 5 liters per minute. While the internal temperature in this case was kept at 100° C., the bottle was shaken for 1 minutes at intervals of 5 minutes to stir the content, thereby bringing the ethylmethylimidazolium $BF_4$ and $N_2$ gas into sufficient contact with each other. This shaking operation was made for 30 minutes.

Thereafter, the fluororesin bottle was taken out from the oil bath, and was cooled to room temperature while $N_2$ gas was caused to flow into the bottle. After the treatment, the water content in the ethylmethylimidazolium $BF_4$ was measured. As a result, it was 400 ppm.

Example 2

Hydrofluoric acid of 50% by weight concentration was added to calcium hydroxide to set the amount of the hydrofluoric acid to a 1.03-fold equivalent of the calcium hydroxide. The components were stirred to produce a liquid suspension of calcium fluoride ($CaF_2$). This suspension of calcium fluoride was filtrated and washed to yield 900 g of calcium fluoride containing 45% by weight of water.

Next, the calcium fluoride was dried at a temperature of 105° C. in the air for 8 hours. The content of oxygen atoms in the dried calcium fluoride was 1500 ppm.

The dried calcium fluoride was burned at 500° C. in a $N_2$ gas flow for 8 hours. Thereafter, the calcium fluoride was cooled to room temperature. The content of oxygen atoms therein was again measured. As a result, the content was 880 ppm.

Into a fluororesin bottle to which a gas intake cock and an exhaust cock were connected was put 200 g of the burned calcium fluoride. Next, the gas intake cock was opened to fill, thereinto, 30% by volume $COF_2$ gas, which was diluted with $N_2$ gas having a water content of 1 ppm or less. Thereafter, the cock was closed. The use amount of the $COF_2$ gas was set to a 10-fold equivalent of oxygen atoms in the water.

Furthermore, the fluororesin bottle was soaked into an oil bath, and heated to set the internal temperature to 130° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 130° C. The bottle was again taken out from the oil bath, and then shaken for one minute to stir the content. This operation was repeated for 2 hours.

Thereafter, the fluororesin bottle was taken out from the oil bath, and was cooled to room temperature while the $COF_2$ gas remaining in the bottle was substituted with $N_2$ gas. After the treatment, the water content in the calcium fluoride was measured. As a result, it was 160 ppm.

Example 3

Hydrofluoric acid of 50% by weight concentration was added to calcium hydroxide to set the amount of the hydrofluoric acid to a 1.03-fold equivalent of the calcium hydroxide. The components were stirred to produce a liquid suspension of calcium fluoride ($CaF_2$). This suspension of calcium fluoride was filtrated and washed to yield 900 g of calcium fluoride containing 45% by weight of water.

Next, the calcium fluoride was dried at a temperature of 105° C. in the air for 8 hours. The content of oxygen atoms in the dried calcium fluoride was measured. As a result, it was 1500 ppm.

The dried calcium fluoride was burned at 500° C. in a $N_2$ gas flow for 8 hours. Thereafter, the calcium fluoride was cooled to room temperature. The content of oxygen atoms therein was again measured. As a result, the content was 880 ppm.

Into a fluororesin bottle to which a gas intake cock and an exhaust cock were connected was put 200 g of the burned calcium fluoride. Next, the gas intake cock was opened to fill, thereinto, 40% by volume $COF_2$ gas, which was diluted with HF gas having a water content of 5 ppm or less. Thereafter, the cock was closed. The use amount of the $COF_2$ gas was set to a 10-fold equivalent of oxygen atoms in the water.

Furthermore, the fluororesin bottle was soaked into an oil bath, and heated to set the internal temperature to 130° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 130° C. The bottle was again taken out from the oil bath, and then shaken for one minute to stir the content. This operation was repeated for 2 hours.

Thereafter, the fluororesin bottle was taken out from the oil bath, and was cooled to room temperature while the HF gas and the $COF_2$ gas in the bottle were substituted with $N_2$ gas. After the treatment, the water content in the calcium fluoride was measured. As a result, it was 90 ppm.

Example 4

Hydrofluoric acid of 50% by weight concentration was added to calcium carbonate to set the amount of the hydrofluoric acid to a 1.03-fold equivalent of the calcium carbonate. The components were stirred to produce a liquid suspension of calcium fluoride ($CaF_2$). This was filtrated and washed to yield 450 g of calcium fluoride containing 10% by weight of water.

Next, the calcium fluoride was dried at a temperature of 105° C. in the air for 8 hours. The content of oxygen atoms and that of carbon atoms in the dried calcium fluoride were measured. The contents were 2600 ppm and 600 ppm, respectively.

The dried calcium fluoride was burned at 500° C. in a $N_2$ gas flow for 8 hours. Thereafter, the calcium fluoride was cooled to room temperature. The content of oxygen atoms and that of carbon atoms therein were again measured. As a result, the contents were 2400 ppm and 560 ppm, respectively.

Into a fluororesin bottle to which a gas intake cock and an exhaust cock were connected was put 200 g of the burned calcium fluoride. Next, the gas intake cock was opened to fill, thereinto, 35% by volume $COF_2$ gas, which was diluted with $N_2$ gas having a water content of 1 ppm or less. Thereafter, the cock was closed. The use amount of the $COF_2$ gas was set to a 10-fold equivalent of oxygen atoms in the water.

Furthermore, the fluororesin bottle was soaked into an oil bath, and heated to set the internal temperature to 130° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 130° C. The bottle was again taken out from the oil bath, and then shaken for one minute to stir the content. This operation was repeated for 2 hours.

Thereafter, the fluororesin bottle was taken out from the oil bath, and was cooled to room temperature while $COF_2$ gas remaining in the bottle was substituted with $N_2$ gas. After the treatment, the content of oxygen atoms and that of carbon atoms in the calcium fluoride were measured. As a result, the contents were 400 ppm and 100 ppm, respectively.

Example 5

Into a 1 L of stainless steel container to which a valve and a pressure meter were connected, was put 500 mL of anhydrous hydrofluoric acid liquid containing 1200 ppm of water as an impurity, and then the container was cooled to 5° C. with an ice bath.

Next, $COF_2$ gas diluted into 50% by volume with $N_2$ was introduced into the stainless steel container. The introduction of $N_2$ gas and $COF_2$ gas was continued until the pressure meter turned to 0.5 MPa. Thereafter, the valve was closed, and the container was allowed to stand still for one hour.

Thereafter, the anhydrous hydrofluoric liquid was sampled from the stainless steel container, and the water content therein was measured. As a result, the content was 3 ppm.

Example 6

First, 200 g of lithium borofluoride ($LiBF_4$) containing 300 ppm of boric acid ($H_3PO_3$) and 200 ppm of water as impurities was put into a fluororesin bottle to which a gas intake cock and an exhaust cock were connected.

Next, the gas intake cock was opened to fill, thereinto, 75% by volume $COF_2$ gas, which was diluted with $N_2$ gas having a water content of 10 ppm or less. Thereafter, the cock was closed. The use amount of the $COF_2$ gas was set to a 5-fold equivalent of oxygen atoms in the whole of the boric acid and the water.

Furthermore, the fluororesin bottle was soaked into an oil bath, and heated to set the internal temperature to 130° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 130° C. The bottle was again taken out from the oil bath, and the bottle was shaken for one minute. This operation was repeated for one hour.

Thereafter, the fluororesin bottle was taken out from the oil bath, and was cooled to room temperature while $COF_2$ gas remaining in the bottle was substituted with $N_2$ gas. After the treatment, the concentration of boric acid and the water content in the lithium borofluoride were measured. As a result, the concentration and the content were 50 ppm and 30 ppm, respectively.

Comparative Example 3

First, 200 g of lithium borofluoride ($LiBF_4$) containing 300 ppm of boric acid ($H_3PO_3$) and 200 ppm of water as impurities was put into a fluororesin bottle to which a gas intake cock and an exhaust cock were connected.

Next, $N_2$ gas having a water content of 1 ppm or less was caused to flow therein by introducing the gas thereinto from the gas intake cock at a gas flow rate of 5 liters per minute and further carrying out exhaust from the exhaust cock. Furthermore, while the $N_2$ gas was caused to flow, the bottle was soaked into an oil bath so as to be heated. While the internal temperature in this case was kept at 130° C., the bottle was shaken for one minute at intervals of five minutes to stir the content, thereby bringing the lithium borofluoride and the $N_2$ gas into sufficient contact with each other. This stirring operation was conducted for one hour.

Thereafter, the fluororesin bottle was taken out from the oil bath, and was cooled to room temperature while $N_2$ gas was caused to flow into the bottle. After the treatment, the concentration of boric acid and the water content in the lithium borofluoride were measured. As a result, the concentration and the content were 300 ppm and 150 ppm, respectively.

Example 7

First, 700 g of triethylmethyl $PF_6$ containing 500 ppm of triethylmethyl $PO_2F_2$ as an impurity was put into a fluororesin bottle to which a gas intake cock and an exhaust cock were connected.

Next, the gas intake cock was opened to fill, thereinto, 45% by volume $COF_2$ gas, which was diluted with $N_2$ gas having a water content of 1 ppm or less. Thereafter, the cock was closed. The use amount of the $COF_2$ gas was set to a 10-fold equivalent of oxygen atoms in the triethylmethyl $PO_2F_2$.

Furthermore, the fluororesin bottle was soaked into an oil bath, and heated to set the internal temperature to 130° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 130° C. The bottle was again taken out from the oil bath, and the bottle was shaken for one minute to stir the content. This operation was repeated for one hour.

Contact was caused. This stirring operation was conducted for one hour.

Thereafter, the fluororesin bottle was taken out from the oil bath, and was cooled to room temperature while $COF_2$ gas remaining in the bottle was substituted with $N_2$ gas. After the treatment, the concentration of triethylmethyl $PO_2F_2$ in the triethylmethyl was measured. As a result, it was 50 ppm.

Example 8

Hydrofluoric acid of 50% by weight concentration was added to calcium chloride to set the amount of the hydrofluoric acid to a 0.97-fold equivalent of the calcium chloride. The components were stirred to produce a liquid suspension of calcium fluoride ($CaF_2$). This was filtrated and washed to yield 500 g of calcium fluoride containing 50% by weight of water.

Next, the calcium fluoride was dried at a temperature of 105° C. in the air for 8 hours. The content of oxygen atoms and that of chlorine atoms in the dried calcium fluoride were each measured. The contents were 2600 ppm and 1700 ppm, respectively. It was presumed that in the state that calcium chloride n hydrates ($4 \leq n \leq 6$) and adhesive moisture were mixed, they were present in the dry calcium fluoride.

Into a fluororesin bottle to which a gas intake cock and an exhaust cock were connected was put 200 g of the dried calcium fluoride. Next, 30% by volume $COF_2$ gas diluted with HF gas having a water content of 1 ppm or less was caused to flow therein by introducing the gas thereinto from the gas intake cock at a gas flow rate of 200 mL per minute and further carrying out exhaust from the exhaust cock. Furthermore, while the $COF_2$ gas was caused to flow, the bottle was soaked into an oil bath so as to be heated. The internal temperature at this time was set to 105° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 105° C. The bottle was again taken out from the oil bath, and then shaken for one minute to stir the content. This operation was repeated for 3 hours.

Thereafter, the fluororesin bottle was taken out from the oil bath, and was cooled to room temperature while $COF_2$ gas was caused to flow into the bottle. After the treatment, the water content and the content of chlorine atoms in the calcium fluoride were measured. As a result, the contents were 450 ppm and 270 ppm, respectively.

Example 9

Two hundred grams of tetraethylammonium $BF_4$ containing 500 ppm of water as an impurity was kept at 2° C. in an ice bath, and the tetraethylammonium $BF_4$ was dissolved into anhydrous hydrofluoric acid the amount of which was equal to that of the $BF_4$ salt.

Next, the gas intake cock was opened to fill, thereinto, 45% by volume $COF_2$ gas, which was diluted with $N_2$ gas having a water content of 1 ppm or less. Thereafter, the cock was closed. The use amount of the $COF_2$ gas was set to a 10-fold equivalent of oxygen atoms in water in the tetraethylammonium $BF_4$. Furthermore, the fluororesin bottle was shaken at 2° C. for 2 hours.

After the reaction ended, the bottle was soaked into an oil bath so as to be heated to 105° C. while $N_2$ gas having a water content of 10 ppm or less was caused to flow into the fluororesin bottle at a rate of 1 liter per minute. In this way, anhydrous hydrofluoric acid was evaporated. Furthermore, while the bottle was shaken for one minute at intervals of five minutes to stir the content in the state that the temperature of the inside of the bottle was kept at 105° C., the $N_2$ gas was caused to flow thereinto for 2 hours. In this way, HF gas was completely purged. Thereafter, the fluororesin bottle was taken from the oil bath and cooled to room temperature. After the treatment, the water content in the tetraethylammonium $BF_4$ was measured. As a result, it was 30 ppm.

Comparative Example 4

Two hundred grams of tetraethylammonium $BF_4$ containing 500 ppm of water as an impurity was kept at 2° C. in an ice bath, and the tetraethylammonium $BF_4$ was dissolved into anhydrous hydrofluoric acid the amount of which was equal to that of the $BF_4$ salt.

Next, the gas intake cock was opened to fill, thereinto, $N_2$ gas having a water content of 1 ppm or less. Thereafter, the cock was closed. The use amount of the $N_2$ gas was set to 2L. Furthermore, the fluororesin bottle was shaken at 2° C. for 2 hours.

After the reaction ended, the bottle was soaked into an oil bath so as to be heated to 105° C. while $N_2$ gas having a water content of 10 ppm or less was caused to flow into the fluororesin bottle at a rate of 1 liter per minute. In this way, anhydrous hydrofluoric acid was evaporated. Furthermore, while the bottle was shaken for one minute at intervals of five minutes to stir the content in the state that the temperature of the inside of the bottle was kept at 105° C., the $N_2$ gas was caused to flow thereinto for 2 hours. In this way, HF gas was completely purged. Thereafter, the fluororesin bottle was taken from the oil bath and cooled to room temperature. After the treatment, the water content in the tetraethylammonium $BF_4$ was measured. As a result, it was 400 ppm.

Example 10

First, 250 g of tetraethylammonium $BF_4$ containing 500 ppm of water as an impurity was put into a fluororesin bottle. The fluororesin bottle was closed with a lid provided with an air intake/exhaust tube having a sealing cock.

Next, it was confirmed by use of $N_2$ gas that no gas leaked from a gap between the fluororesin bottle and the lid. Thereafter, 50% by volume $COF_2$ gas was filled thereinto, and then the cock was closed to seal the bottle. The use amount of the $COF_2$ gas was set to a 3-fold equivalent of oxygen atoms in the water.

Furthermore, the fluororesin bottle was soaked into an oil bath, and heated to set the internal temperature to 50° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 50° C. The bottle was again taken out from the oil bath, and the bottle was shaken for one minute to stir the content. This operation was repeated for one hour.

Thereafter, the fluororesin bottle was taken out from the oil bath, and was cooled to room temperature while $COF_2$ gas remaining in the bottle was substituted with $N_2$ gas. After the treatment, the concentration of the content of water (which had reacted with $BF_4$ to be present as $H_3BO_3$) in the tetraethylammonium $BF_4$ was measured. As a result, it was 200 ppm.

Comparative Example 5

First, 250 g of tetraethylammonium $BF_4$ containing 500 ppm of water as an impurity was put into a fluororesin bottle. The fluororesin bottle was closed with a lid provided with an air intake/exhaust tube having a sealing cock.

Next, it was confirmed by use of $N_2$ gas that no gas leaked from a gap between the fluororesin bottle and the lid. Thereafter, 50% by volume $COF_2$ gas was filled thereinto, and then the cock was closed to seal the bottle. The use amount of the $COF_2$ gas was set to a 0.05-fold equivalent of oxygen atoms in the water.

Furthermore, the fluororesin bottle was soaked into an oil bath, and heated to set the internal temperature to 100° C. Thereafter, the fluororesin bottle was taken out from the oil bath, and the bottle was shaken for one minute to stir the content. Thereafter, the bottle was returned into the oil bath, and soaked therein for about 5 minutes until the internal temperature turned to 50° C. The bottle was again taken out from the oil bath, and the bottle was shaken for one minute to stir the content. This operation was repeated for one hour.

Thereafter, the fluororesin bottle was taken out from the oil bath, and was cooled to room temperature while $COF_2$ gas remaining in the bottle was substituted with $N_2$ gas. After the treatment, the concentration of the content of water (which had reacted with $BF_4$ to be present as $H_3BO_3$) in the tetraethylammonium $BF_4$ was measured. As a result, it was 500 ppm.

The invention claimed is:

1. A process for purifying a fluorine compound from a composition comprising said fluorine compound and an oxygen compound comprising bringing carbonyl fluoride into contact with the composition, thereby removing at least oxygen from the composition, wherein the carbonyl fluoride is present in a molar amount from 0.1 to 100 times the molar amount of oxygen atoms in the oxygen compound, and the fluorine compound is a fluoride salt.

2. The process for purifying a fluorine compound according to claim 1, wherein the contact between the fluorine compound and the carbonyl fluoride is performed at a temperature ranging from −50 to 500° C.

3. The process for purifying a fluorine compound according to claim 1, wherein the contact between the fluorine compound and the carbonyl fluoride is performed by direct contact therebetween in the absence of any solvent.

4. The process for purifying a fluorine compound according to claim 1, wherein the carbonyl fluoride is in a gaseous form and is diluted with an inactive gas having a water content of 10 ppm or less to set the content of carbonyl fluoride into the range of 0.01% or more by volume and less than 100% by volume.

5. The process for purifying a fluorine compound according to claim 4, wherein the inactive gas is at least one selected from the group consisting of $CO_2$, HF, $N_2$, He, Ne, Ar and dry air.

6. The process for purifying a fluorine compound according to claim 1, wherein the contact between the fluorine compound and the carbonyl fluoride is performed at a pressure ranging from 0.2 KPa to 1 MPa.

7. The process for purifying a fluorine compound according to claim 1, wherein the fluorine compound is brought into contact with the carbonyl fluoride in the state that the fluorine compound is dissolved or dispersed in a solvent.

8. The process for purifying a fluorine compound according to claim 7, wherein the solvent is a solvent which is neither reactive with the carbonyl fluoride nor the fluorine compound.

9. The process for purifying a fluorine compound according to claim 1, wherein the concentration of the oxygen compound contained in the fluorine compound is less than 10% by weight.

10. The process for purifying a fluorine compound according to claim 1, wherein said fluoride salt is selected from the group consisting of fluorides of a rare earth element and fluoride complex salts.

* * * * *

UNITED STATES PATENT AND TRADEMARK OFFICE
CERTIFICATE OF CORRECTION

PATENT NO. : 8,232,436 B2
APPLICATION NO. : 12/443877
DATED : July 31, 2012
INVENTOR(S) : Waki et al.

It is certified that error appears in the above-identified patent and that said Letters Patent is hereby corrected as shown below:

On the Title page (item 56) at line 18, Under Other Publications, change "Chemity," to --Chemistry,--.

On the Title page (item 56) at line 19, Under Other Publications, change "Mosco; Inorg." to --Moscow; Inorg.--.

On the Title page (item 56) at line 22, Under Other Publications, change "Chiniese" to --Chinese--.

In column 1 at line 5, Change "Internationl" to --International--.

In column 4 at line 12, Change "$K_3NiF7$, $k_2TiF_6$," to --$K_3NiF_7$, $K_2TiF_6$,--.

Signed and Sealed this
Eighth Day of January, 2013

David J. Kappos
*Director of the United States Patent and Trademark Office*